United States Patent [19]

Sandel

[11] Patent Number: 4,524,006

[45] Date of Patent: Jun. 18, 1985

[54] SELECTED ALKYLHYDRAZINE AND HYDROXYALKYLHYDRAZINE ADDUCTS OF DIISOCYANATES AND THEIR USE AS ANTIOXIDANTS

[75] Inventor: Bonnie B. Sandel, Milford, Conn.

[73] Assignee: Olin Corporation, Cheshire, Conn.

[21] Appl. No.: 610,908

[22] Filed: May 16, 1984

[51] Int. Cl.$^3$ .............................................. C10M 1/32
[52] U.S. Cl. .................................. 252/51.5 A; 44/64; 44/71; 44/72; 252/403
[58] Field of Search ............... 44/71, 72, 64; 252/403, 252/51.5 A; 564/34

[56] References Cited

U.S. PATENT DOCUMENTS

| | | | |
|---|---|---|---|
| 1,906,044 | 4/1933 | Burk . | |
| 2,328,190 | 8/1943 | Burk et al. | 44/74 |
| 2,580,881 | 1/1952 | Biswell | 252/42.4 |
| 2,683,083 | 7/1954 | Hill et al. | 252/403 |
| 2,710,841 | 6/1955 | Swakon et al. | 252/51.5 A |
| 2,729,690 | 1/1956 | Oldenburg | 260/799 |
| 2,785,965 | 3/1957 | Hill et al. | 252/403 |
| 2,993,044 | 7/1961 | Applegath et al. | 252/51.5 A |
| 3,403,013 | 9/1968 | Eckert | 44/71 |
| 3,489,684 | 1/1970 | O'Shea | 252/51.5 |
| 3,632,600 | 1/1972 | Morris | 260/383 |
| 3,773,722 | 11/1973 | Dexter | 260/45.75 |

OTHER PUBLICATIONS

U.S. Patent Application Ser. No. 560,721 filed by B. B. Sandel on Dec. 12, 1983.

C. Collard-Charon and M. Renson, Chemical Abstracts 59, 8270(g).
C. Zinner et al., Chemical Abstracts 78, 97543(a).
C. Vogelesang, Chemical Abstracts, 39, 1393(8).
M. Ward et al., Chemical Abstracts, 49, 1815(e).
Olin Literature Search for Bis-Semicarbazides of Various Diisocyanates.

*Primary Examiner*—Y. Harris-Smith
*Attorney, Agent, or Firm*—William A. Simons; Thomas P. O'Day

[57] ABSTRACT

Disclosed are selected alkylhydrazine and hydroxyalkylhydrazine adducts of diisocyanates having the formula

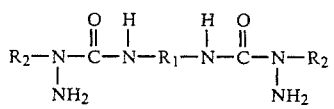

wherein $R_1$ is selected from the group consisting of an arylene group containing from 6 to about 12 carbon atoms and a cycloalkylene group containing from about 5 to about 20 carbon atoms; and wherein $R_2$ is selected from the group consisting of alkyl group containing from 1 to about 20 carbon atoms and hydroxyalkyl group containing from 2 to about 20 carbon atoms. These compounds have utility as antioxidants for a variety of organic compounds subject to oxidative degradation, including functional fluids such as petroleum fuels and lubricants.

17 Claims, No Drawings

SELECTED ALKYLHYDRAZINE AND HYDROXYALKYLHYDRAZINE ADDUCTS OF DIISOCYANATES AND THEIR USE AS ANTIOXIDANTS

BACKGROUND OF THE INVENTION

1. Field of the Invention

The present invention relates to selected alkylhydrazine and hydroxyalkylhydrazine adducts of diisocyanates and their use as antioxidants.

2. Brief Description of the Prior Art

Organic compositions containing olefinic and other linkages susceptible to oxidation will degrade when exposed to air. In the case of petroleum fuels such as gasoline, this autoxidation may lead to undesirable gum formation and to the formation of polar materials which may contribute to the corrosive properties of the fuel. Antioxidant chemicals may be added to these organic compositions to decrease the rate of this undesirable oxidative deterioration.

Numerous compounds have been disclosed as useful as antioxidants. For example, several classes of hydrazine derivatives have been described as antioxidants. U.S. Pat. No. 1,906,044 (issued to Burk on Apr. 25, 1933) teaches that semicarbazide, 4,4-disubstituted semicarbazides and certain aromatic hydrazines have an antigumming behavior in petroleum fuels. U.S. Pat. No. 2,328,190 (issued to Burk et al. on Aug. 31, 1943) teaches that certain thiocarbazides and thiosemicarbazides containing aryl substitutents act as antioxidants in fuels.

U.S. Pat. No. 2,580,881 (issued to Biswell on Jan. 1, 1952) teaches that certain salts of the 1-(ortho-hydroxyarylidene)-aminoguanidines are antioxidants.

Zinner et al, Arch. Parm., Weinheim, Germany, 1973, 306(1), 35–44, disclose the reaction of methylhydrazine with certain substituted isocyanates to yield certain disubstituted semicarbazides. However, no utility for these compounds is disclosed. U.S. Pat. No. 2,656,350 discloses the preparation of 5-nitro-2-furaldehyde 2-(2-hydroxyethyl)-4-methylsemicarbazone. No utility as an antioxidant is recognized.

There is a need for new antioxidants which have improved effectiveness in a wide variety of applications.

It is a primary object of this invention to provide improved antioxidant compositions.

It is a further object of this invention to provide certain novel alkylhydrazine and hydroxyalkylhydrazine adducts of diisocyanate compositions useful as antioxidants.

Still another object of this invention is to provide a method of inhibiting the oxidative degradation of organic compounds.

These and other objects of the invention will be apparent from the following detailed description of the invention.

BRIEF SUMMARY OF THE INVENTION

The foregoing objects are accomplished in the present invention which is directed to antioxidant compositions comprised of alkylhydrazine and hydroxyalkylhydrazine adducts of diisocyanates having the formula (I):

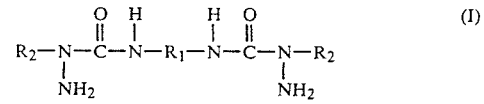

wherein $R_1$ is selected from the group consisting of an arylene group containing from 6 to about 12 carbon atoms and a cycloalkylene group containing from about 5 to about 20 carbon atoms; and wherein $R_2$ is selected from the group consisting of an alkyl group containing from 1 to about 20 carbon atoms, and a hydroxyalkyl group containing from 2 to about 20 carbon atoms. The present invention is also directed to the method of using these alkylhydrazine and hydroxyalkylhydrazine adducts of diisocyanates as antioxidants in organic compounds subject to oxidative degradation including functional fluids, such as petroleum fuels or lubricants.

Another embodiment of this invention is directed to the compounds of formula (I) as novel compositions-of-matter.

DETAILED DESCRIPTION

The alkylhydrazine and hydroxyalkylhydrazine adducts of diisocyanates of the present invention are made by reacting a selected diisocyanate with a selected substituted hydrazine, preferably in the presence of an inert solvent. This reaction is illustrated by the following Equation (A):

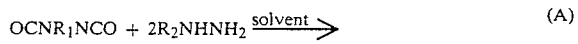

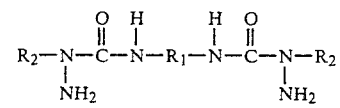

These adducts of the present invention may be alternatively called bis(alkylhydrazinecarboxamides) or bis(hydroxyalkylhydrazinecarboxamides).

Suitable substituted diisocyanates for reaction A, where $R_1$ is an arylene group having from 6 to about 12 carbon atoms and, preferably containing one benzene ring, include phenylene-1,2-diisocyanate, phenylene-1,3-diisocyanate, phenylene-1,4-diisocyanate, tolylene-2,4-diisocyanate, tolylene-2,3-diisocyanate, tolylene-3,4-diisocyanate, tolylene-2,6-diisocyanate, tolylene-2,5-diisocyanate, tolylene-3,5-diisocyanate, and m- or p-tetramethylxylenediisocyanate and the like.

Suitable substituted diisocyanates where $R_1$ is a cycloalkylene group having about 5 to about 20 carbon atoms include cyclohexyl-1,2-diisocyanate, cyclohexyl-1,3-diisocyanate, cyclohexyl-1,4-diisocyanate, isophorone-diisocyanate, 3-methylcyclohexyl-1,2-diisocyanate, 4-methylcyclohexyl-1,2-diisocyanate, 5-methylcyclohexyl-1,2-diisocyanate, 2-methylcyclohexyl-1,3-diisocyanate, 4-methylcyclohexyl-1,3-diisocyanate, 5-methylcyclohexyl-1,3-diisocyanate, 2-methylcyclohexyl-1,4-diisocyanate, bis(4-isocyanatocyclohexyl)methane and its isomers, cyclopentyl diisocyanates, cycloheptyl diisocyanates, bicyclodecyl diisocyanates, isomers thereof and the like.

The preferred substituted diisocyanates are those where $R_1$ is a cycloalkylene group having from about 6 to about 15 carbon atoms. Cycloalkylene diisocyanates are preferred because of their better compatibility with hydrocarbons than their arylene counterparts.

Suitable substituted hydrazine reactants for reaction A, where $R_2$ is an alkyl group having from 1 to about 20 carbon atoms include lower alkyl substituted hydrazine such as methylhydrazine, ethylhydrazine, propylhydrazine, isobutylhydrazine, n-butylhydrazine, t-butylhydrazine, n-pentylhydrazine, neopentylhydrazine, and higher alkyl-substituted hydrazines such as hexylhydrazine, octylkydrazine, decylhydrazine, dodecylhydrazine, tetradecylhydrazine, octadecyl hydrazine and the like. Suitable substituted hydrazines where $R_2$ is a hydroxyalkyl group having from 2 to about 20 carbon atoms include 2-hydroxethylhydrazine, 2-hydroxypropylhydrazine, 2-hydroxybutylhydrazine, 3-hydroxypropylhydrazine, 3-hydroxy-2-butylhydrazine and the like.

The preferred substituted hydrazines have as an $R_2$ substituent either an alkyl group containing from 1 to about 8 carbon atoms or a hydroxyalkyl group containing from 2 to about 6 carbon atoms. Alternatively the acid salt of the substituted hydrazine may be used as a reactant provided sufficient base is added to liberate the free substituted hydrazine.

Preferably, this reaction is carried out in the presence of inert organic solvents such as tetrahydrofuran, diethyl ether, petroleum ether, toluene, benzene, dioxane, hexane, heptane, isooctane, xylene and mixtures thereof. The amount of solvent employed is not critical to the present invention and any conventional amounts may be used. For most reactions, the weight ratio of solvent to total reactants is preferably from about 5:1 to about 50:1.

Any conventional reaction conditions designed to produce alkylhydrazine and hydroxyalkylhydrazine adducts of diisocyanates in accordance with Equation (A) may be employed in the synthesis of the antioxidant compounds of this invention. The present invention is not intended to be limited to any particular reaction conditions.

When preparing the compounds of this invention according to the reaction illustrated by Equation (A) in the presence of an inert solvent, the molar ratio of the substituted hydrazine to the diisocyanate is at least about 1.8:1 to ensure a desired yield of the resulting antioxidant product. Preferably, this mole ratio is in the range from about 2:1 to about 3:1.

Both the reaction temperature and time will depend upon many factors including the specific reactants and apparatus employed. In most situations, reaction temperatures from about 0° C. to about 100° C. may be employed. The reaction temperatures for the reaction illustrated by Equation (A) are preferably from about 15° C. to about 50° C. Reaction times may range from about 0.5 hour to about 24 hours. The reaction time will also depend upon the reaction temperatures chosen. The reaction pressure is preferably atmospheric; although subatmospheric (e.g., down to about 200 mm Hg) and superatmospheric (e.g., up to about 10 atmospheres) pressures may be useful in some situations. The desired products of the present invention may be removed from the reaction mixture by any suitable means, including evaporation of the solvent, filtration, extraction, recrystallization, distillation, or the like.

One specific preferred procedure for preparing the compounds of the present invention is to first prepare individual solutions of each reactant in the same solvent. The solution of the selected diisocyanate reactant is then preferably added to the solution containing the desired substituted hydrazine. The combined solutions are stirred with or without heating until the reaction is complete. The alkylhydrazine and hydroxyalkylhydrazine adducts of diisocyanate product may precipitate when a hydrocarbon or an ether solvent (e.g. benzene, toluene, petroleum ethers or mixtures of these) are employed. The precipitated product is recovered by conventional techniques such as filtration or recrystallation or the like.

It should be noted that while the reaction illustrated by Equation (A) is the preferred method for preparing the compounds of the present invention, other methods of preparation may also be employed.

Also, in accordance with the present invention, the compounds of Formula I, above, may be utilized as effective oxidation inhibitors or antioxidants. In practicing the process of the present invention, an effective oxidation-inhibiting amount of one or more of these compounds is added to an organic composition subject to oxidation degradation such as a functional fluid, polyolefin plastics, or the like. It is understood that the term "effective oxidation-inhibiting amount" as used in the specification and claims herein is intended to include any amount that will prevent or control the oxidation of said organic composition. Of course, this amount may be constantly changing because of the possible variations in many parameters. Some of these parameters may include the specific base fluid to be protected; the salt and oxygen content of the system; the specific compound of the present invention used as an antioxidant; the geometry and capacity of the system to be protected; temperature; and the like.

The antioxidant compounds of this invention may be preferably used in concentrations ranging from about 0.0001% to about 10% by weight of the organic composition. More preferably, this concentration may range from about 0.005% to about 2% by weight of the organic composition. Functional fluids in which the antioxidant compounds of this invention may be added include hydrocarbon distillate fuels, hydrocarbon lubricant oils and greases, and non-hydrocarbon (i.e. synthetic oil base stocks) distillate fuels, lubricant oils and greases. The latter may include non-hydrocarbon compounds such as phosphate esters, carbonate esters, silicones, silicate esters, alkoxysilane cluster compounds, polyglycols, glycol esters and the like. The foregoing functional fluids may be used as fuels, lubricating oils, hydraulic fluids, brake fluids, heat transfer fluids, and the like. Polyolefins such as polyethylene, polypropylene, polybutadiene, and the like as well as styrenics such as polystyrene, ABS and IPS may also be inhibited against oxidative degradation with the antioxidants of this invention.

One preferred class of functional fluids is liquid hydrocarbon fuels such as gasoline or diesel fuel. Another preferred class of functional fluids is hydrocarbon lubricants. For example, a liquid hydrocarbon fuel or lubricant may comprise a base fuel such as gasoline, or diesel fuel, or a base hydrocarbon lubricant such as grease mixed with an effective oxidation-inhibiting amount of one or more of the compounds of Formula (I) to inhibit oxidation of the functional fluid.

Various known inhibitors and additives may also be added with the antioxidant compounds of this invention to the organic composition such as functional fluids. These other additives and inhibitors further control or modify various chemical and physical properties of the functional fluids. The general term "inhibitor" is used for those additives which increase resistance to chemical changes. The ultimate function of an inhibitor is to maintain both the mechanical parts of the system and the fluid as close to their original conditions as possible.

Included among the various types of other additives which can be added to the functional fluids of this invention are: inhibitors for pH and corrosion control, other antioxidants, rust inhibitors, viscosity-index improvers, pour-point depressants, wear additives, lubricating additives, anti-foamants, metal deactivators, metal passivators, stabilizers, demulsifiers, dyes, and odor supressants. Generally, the total amount of other additives which may be incorporated into the fluid composition will vary depending on the particular composition and the desired properties. More particularly, the total amount of other additives will comprise from 0 to 20 percent and preferably from 0.1 to 8.0 percent by weight based on the total weight of the fluid composition.

The antioxidants of this invention are effective at low concentrations, imparting to hydrocarbons greater color stability than previously known alkylated p-phenylenediamine antioxidants available commercially while still preventing gum formation and are more useful than other known hydrazinecarboxamides in lubricant applications where their lower volatility is desired. They are also compatible with and impart oxidation stability to compositions containing alcohols, such as gasoline/ethanol, gasoline/t-butanol, or gasoline/methanol blends. In addition to being more hydrocarbon compatible than semicarbazide, the adducts of this invention are also more effective at preventing oxidative degradation.

The following Examples illustrate various embodiments of the present invention. All parts and percentages are by weight unless explicitly stated otherwise.

EXAMPLE 1

N,N'-(Methylenedi-4-cyclohexyl-1-ylidene)-bis(1-methylhydrazinecarboxamide)

To methylhydrazine 12 ml (0.22 moles) in 100 ml toluene was added dropwise with stirring bis(4-isocyanatocyclohexyl)methane [1] (26.2 g, 0.1 moles) in 100 ml toluene. After addition was complete, the solution was heated under reflux for one hour then stirred overnight at room temperature. The precipitated product was collected by suction filtration in quantitative yield. Recrystallization from benzene: ethanol (68:32 by volume) afforded a white powder with m.p. 187°–193° C. NMR analysis confirmed the structure.

[1] H$_{12}$MDI is manufactured by Mobay Chemical Corporation of Pittsburgh, PA under the trademark Desmodur W.

EXAMPLE 2

N,N'-(4-Methyl-1,3-phenylene)bis(1-methylhydrazinecarboxamide)

To methylhydrazine 11.2 ml (0.21 mole) in 100 ml tetrahydrofuran was added dropwise with stirring tolylene-2,4-diisocyanate 14.2 ml (0.10 mole) in 40 ml of THF. The solution immediately warmed as precipitation began. Stirring was continued overnight at ambient temperature. The mixture was filtered and the precipitate washed with tetrahydrofuran. Both the precipitate and the residue after evaporation of the solvent gave similar IR spectra. They were combined to afford a quantitative yield of the crude product. Recrystallization from methanol affords a white powder, m.p. 164°–165° C., which was identified as the bis adduct by NMR analysis.

EXAMPLE 3

N-[1-[1-(2-Hydroxyethyl)hydrazinecarboxamido]methyl1,3,3-trimethyl-5-cyclohexyl]-1-(2-hydroxyethyl)-hydrazinecarboxamide To a rapidly stirred mixture of 2-hydroxyethylhydrazine 16.74 g (0.22 moles) in 250 ml tetrahydrofuran was added dropwise isophorone diisocyanate [2] in 0.10 moles (22.23 g) in 180 ml tetrahydrofuran. After addition was complete, the solution was clear and colorless. The solution was stirred for an additional three hours at room temperature. The solvent was removed by rotary evaporation to yield a colorless syrup. Characterization by IR and NMR showed it to be predominantly the postulated structure. The sample was utilized without further purification in screening for antioxidant effectiveness.

Elemental Analysis: Theory 51.32% C, 9.15% H, 22.44% N; Found 52.24% C, 9.05% H, 19.67% N.

[2] IPDI is manufactured by Chemische Werke Huls AG of Marl, West Germany.

EXAMPLES 4–6

Induction Period Measurement

Examples of the compounds in Examples 1–3 were weighed and individually dissolved in heptane/ethanol solutions to prepare stock solutions. Aliquots of these solutions were then added to 40% by volume cyclohexane in heptane to provide test solutions having 10 mg/L concentration of the active compound.

Each test solution was heated under an oxygen atmosphere according to the standard procedures of ASTM D525. The bomb utilized for this measurement was modified for automatic data acquisition by being fitted with a pressure transducer. This transducer was connected to a microprocessor programmed for voltage/time data acquisition. The induction period for each test solution was determined according to its definition in the standard Method ASTM D525.

Results are tabulated in Table I and show these compounds stabilize a hydrocarbon liquid significantly. In each case, the observed induction period is increased greatly over the unstabilized fluid, Comparison A, which indicates the improved stability of the hydrocarbons against oxidative degradation when the antioxidants of this invention are present.

TABLE I

| Induction Period for Cyclohexene/Heptane Solutions | | | |
|---|---|---|---|
| Example | Compound Example | Concentration (mg/L) | Observed Induction Period (min.) |
| Comparison A | none | 0 | 76.2 |
| 4 | 1 | 10.0 | 373 |
| 5 | 2 | 10.0 | 298 |
| 6 | 3 | 10.0 | 209 |

EXAMPLES 7–9

Measurement of Potential Residue

Individual solutions of the compounds made in Examples 1–3 were added to a hydrocarbon mixture containing 60% by volume isooctane, 35% by volume cyclohexane and 5% by volume toluene to provide test solutions having concentrations of 10.00 mg/L of active compounds. The test solutions were heated under an oxygen atmosphere and evaporated in a stream of heated air according to the procedures of ASTM D873.

The amount of gum formed (in mg/100 mL) in the presence of these antioxidants is tabulated below. In all cases the amount of gum formed is reduced significantly relative to the unstabilized base fluid (Comparison B).

TABLE II

| | Total Gum From Isooctane/Cyclohexane/Toluene Solutions | | |
|---|---|---|---|
| Example | Compound Example | Concentration (mg/L) | Total Gum (mg/100 mL) |
| Comparison B | none | 0 | 63 |
| 7 | 1 | 10.0 | 1.14 |
| 8 | 2 | 10.0 | 6.8 |
| 9 | 3 | 10.0 | 2.7 |

What is claimed is:

1. A method for inhibiting the oxidation of functional fluids selected from the group consisting of liquid hydrocarbon distillate fuels and hydrocarbon lubricant oils and greases which comprises adding to said functional fluid an effective oxidation inhibiting amount of an alkylhydrazine or hydroxyalkylhydrazine adduct of a diisocyanate having the formula:

$$R_2-N(NH_2)-C(=O)-N(H)-R_1-N(H)-C(=O)-N(NH_2)-R_2$$

wherein $R_1$ is selected from the group consisting of an arylene group containing from 6 to about 12 carbon atoms and a cycloalkylene group containing from about 5 to about 20 carbon atoms; and wherein each $R_2$ is individually selected from the group consisting of an alkyl group containing from 1 to about 20 carbon atoms and a hydroxyalkyl group containing from 2 to about 20 carbon atoms.

2. The method of claim 1 wherein $R_1$ is a cycloalkylene group containing from about 6 to about 15 carbon atoms.

3. The method of claim 1 wherein $R_2$ is an alkyl group containing from 1 to about 8 carbon atoms.

4. The method of claim 1 wherein $R_2$ is a hydroxyalkyl group containing from 2 to about 6 carbon atoms.

5. The method of claim 1 wherein the effective oxidation inhibiting proportion is from about 0.0001 percent to about 10 percent by weight of the functional fluid.

6. The method of claim 5 wherein the effective oxidation inhibiting proportion is from about 0.005 percent to about 2 percent by weight of the functional fluid.

7. An oxidation-inhibited functional fluid composition comprising a functional base fluid selected from the group consisting of liquid hydrocarbon distillate fuels and hydrocarbon lubricant oils and greases and containing an effective oxidation inhibiting amount of an alkylhydrazine or hydroxyalkylhydrazine adduct of a diisocyanate having the formula:

$$R_2-N(NH_2)-C(=O)-N(H)-R_1-N(H)-C(=O)-N(NH_2)-R_2$$

wherein $R_1$ is selected from the group consisting of an arylene group containing from 6 to about 12 carbon atoms and a cycloalkylene group containing from about 5 to about 20 carbon atoms; and wherein each $R_2$ is individually selected from the group consisting of an alkyl group containing from 1 to about 20 carbon atoms and a hydroxyalkyl group containing from 2 to about 20 carbon atoms.

8. The functional fluid composition of claim 3 wherein said functional base fluid comprises a liquid hydrocarbon distillate fuel.

9. The functional fluid composition of claim 8 wherein said liquid hydrocarbon distillate fuel is gasoline.

10. The functional fluid composition of claim 7 wherein said hydrocarbon distillate fuel is diesel fuel.

11. The functional fluid composition of claim 7 wherein $R_1$ is a cycloalkylene group containing from about 6 to about 15 carbon atoms.

12. The functional fluid composition of claim 7 wherein $R_2$ is an alkyl group containing 1 to about 8 carbon atoms.

13. The functional fluid composition of claim 7 wherein $R_2$ is a hydroxyalkyl group containing 2 to about 6 carbon atoms.

14. An alkylhydrazine or hydroxyalkylhydrazine adduct of a diisocyanate having the formula:

$$R_2-N(NH_2)-C(=O)-N(H)-R_1-N(H)-C(=O)-N(NH_2)-R_2$$

wherein $R_1$ is selected from the group consisting of an arylene group containing from 6 to about 12 carbon atoms and a cycloalkylene group containing from about 5 to about 20 carbon atoms; and wherein $R_2$ is selected from the group consisting of an alkyl group containing from 1 to about 20 carbon atoms and a hydroxyalkyl group containing from 2 to about 20 carbon atoms.

15. The compound of claim 14 wherein $R_1$ is a cycloalkylene group containing from about 6 to about 15 carbon atoms.

16. The compound of claim 14 wherein $R_2$ is an alkyl group containing from 1 to about 8 carbon atoms.

17. The compound of claim 14 wherein $R_2$ is a hydroxyalkyl group containing from 2 to about 6 carbon atoms.

* * * * *

UNITED STATES PATENT AND TRADEMARK OFFICE
CERTIFICATE OF CORRECTION

PATENT NO. : 4,524,006

DATED : June 18, 1985

INVENTOR(S) : Bonnie B. Sandel

It is certified that error appears in the above-identified patent and that said Letters Patent is hereby corrected as shown below:

In column 7, at line 13 "1.14" should be --1.4--.

Signed and Sealed this

Twenty-second Day of October 1985

[SEAL]

Attest:

DONALD J. QUIGG

Attesting Officer

Commissioner of Patents and
Trademarks—Designate